United States Patent [19]

Phillips, Jr. et al.

[11] Patent Number: 5,723,709

[45] Date of Patent: Mar. 3, 1998

[54] TERPENE DIMER COMPOSITIONS AND RELATED METHODS OF MANUFACTURE

[75] Inventors: Claude Frank Phillips, Jr., Lynn Haven; James William Booth, Panama City, both of Fla.

[73] Assignee: Arizona Chemical Company, Panama City, Fla.

[21] Appl. No.: 677,174

[22] Filed: Jul. 9, 1996

Related U.S. Application Data

[63] Continuation of Ser. No. 227,807, Apr. 14, 1994, abandoned.

[51] Int. Cl.$^6$ .............. C07C 2/76; C07C 13/00; C07C 13/28

[52] U.S. Cl. .............. 585/362; 585/10; 585/11; 585/12; 585/16; 585/17; 585/20; 585/21; 585/22; 585/23; 585/350; 585/360; 585/361

[58] Field of Search .............. 585/10, 11, 12, 585/16, 17, 20–23, 350, 360, 361, 362

[56] References Cited

U.S. PATENT DOCUMENTS

| | | | |
|---|---|---|---|
| 2,249,112 | 7/1941 | Carmody | 585/20 |
| 3,401,136 | 9/1968 | Sellers | 524/474 |
| 3,415,769 | 12/1968 | Todd et al. | 524/474 |
| 3,415,893 | 12/1968 | Sellers et al. | 568/827 |
| 3,502,769 | 3/1970 | Fukuhara | 424/47 |
| 3,931,077 | 1/1976 | Uchigaki et al. | 524/272 |
| 4,052,549 | 10/1977 | Booth | 526/237 |
| 4,165,301 | 8/1979 | Wiegers et al. | 512/3 |
| 4,170,576 | 10/1979 | Hall et al. | 512/3 |
| 4,399,249 | 8/1983 | Bildusas | 524/271 |
| 4,922,047 | 5/1990 | Chen et al. | 585/12 |
| 5,092,907 | 3/1992 | Riblet et al. | 8/645 |

OTHER PUBLICATIONS

J. J. Ritter et al. "Acid–Polymerized Dipinene" *J. Am. Chem Soc*, vol. 62, pp. 1508–1511 (1940) no month available.

Roy et al. "Structural Studies on ∝–Pinene Dimers" *J. Indian Chem Soc.*, vol. 49, No. 12, pp. 1222–1238 (1972) no month available.

*Primary Examiner*—Elizabeth D. Wood
*Attorney, Agent, or Firm*—Ostrager, Chong & Flaherty

[57] ABSTRACT

Terpene dimer compositions are provided which dry into a hard, tack free film upon exposure to air. The compositions include a terpene dimer having the molecular formula $C_{20}H_{32}$ and contain at least one double bond. The terpene dimer is derived from a naturally occurring monoterpene, or mixtures thereof, having the molecular formula $C_{10}H_{16}$. In an another embodiment the compositions, in addition to the terpene dimer, include isomers of the monoterpenes. The compositions are substantially free of higher terpene oligomers having molecular formulas greater than $C_{20}H_{32}$. Processes for making the terpene dimer compositions are also provided. Advantageous utilization of these compositions is as a diluent, solvent or component in coating, adhesive, alkyd or ink formulations, as an environmentally safe non-toxic material.

21 Claims, 8 Drawing Sheets

TERPENE DIMER COMPOSITIONS AND RELATED METHODS OF MANUFACTURE

This application is a continuation of application Ser. No. 08/227,807 filed on Apr. 14, 1994, and now abandoned.

FIELD OF INVENTION

This invention generally relates to terpene dimer compositions and methods of making the same. More particularly, it concerns terpene dimer compositions, derived from naturally occurring monoterpenes, which are substantially free of higher terpene oligomers. Upon exposure to air the compositions dry into a hard tack free film.

BACKGROUND ART

Prior art practice has broadly disclosed terpene polymer compositions and methods of manufacture in a variety of applications.

Dipinene, $C_{20}H_{32}$, resulting from the action of acids on alpha- or beta-pinene has been studied by various investigators since its discovery over a century ago by Deville, Ann. Chim. Phys. [2] 75, 66 (1840) and Ann. Chim. 37, 192 (1840) who obtained the substance from turpentine oil and sulfuric acid.

In an article by J. J. Ritter, "J. Am. Chem. Soc.", vol. 62, pp. 1508–09 (1940) the preparation of acid-polymerized dipinene is shown. The disclosure in Ritter is directed to the study of the structure of a dehydrogenated terpene dimer. The process conditions in Ritter for preparing the terpene dimer result in a product that includes more than 15% of higher terpene oligomers.

U.S. Pat. No. 2,249,112 to Carmody discloses a process for the hydrogenation of terpene polymers. Polymerization of the terpenes is effected by a special catalyst—Attapulgus clay—or other catalysts including aluminum chloride, zinc chloride, tin tetrachloride and sulphuric acid. The terpene polymers formed are hydrogenated and saturated.

U.S. Pat. No. 3,401,136 to Sellers discloses dipentene polymer compositions having softening points between 0°–85° C. useful as components of hot melt coating compositions and adhesives. Oligomers of a cyclic monoterpene hydrocarbon, such as dipentene, limonene, α-pinene, or β-pinene, are added to the dipentene polymer in amounts of at least 5% based on the weight of the composition.

U.S. Pat. No. 3,415,769 to Todd et al. discloses ethylene-α-olefin elastomer compositions including oligomers of cyclic monoterpene hydrocarbons as a plasticizer-tackifier. The oligomers have the general formula $(C_{10}H_{16})_n$, wherein n represents an integer in the range of 2 to 8 and have boiling points in the range of 170°–240° C. at 10 mm pressure.

U.S. Pat. No. 3,415,893 to Sellers et al. discloses a process of producing synthetic pine oil from α-pinene and terpene compositions containing α-pinene without formation of terpin hydrate solids. The by-products of the reaction are useful as solvents and are primarily monocyclic hydrocarbons containing some cineols, cyclic ethers and other "undesirable products" of the reaction. The pine oil produced by the process is essentially terpene alcohols including at least 60% of α-terpineol.

U.S. Pat. No. 3,502,769 to Fukuhara discloses a toilet preparation containing a storage stabilizing amount of a monocyclic hydrogenated terpene polymer of the formula $(C_{10}H_{19})_n$ and/or a bicyclic hydrogenated terpene polymer of the formula $(C_{10}H_{17})_n$, where n is a whole number from 2 to 4, in a cosmetic base. The hydrogenated terpenes are produced from alicyclic terpene hydrocarbons.

U.S. Pat. No. 3,931,077 to Uchigaki et al. discloses a reactive hot-melt adhesive composition comprising a reactive urethane prepolymer, a thermoplastic polymer and a tackifier. The tackifier includes a terpene-phenol copolymer where the terpene is a monoterpene having 10 carbon atoms such as α-pinene, β-pinene, dipentene. Diterpene analogs of the monoterpenes having 20 carbon atoms are also used.

U.S. Pat. No. 4,052,549 to Booth discloses terpene polymer compositions useful as components of hot melt coating compositions, adhesives and the like. The resinous terpene polymer composition having a softening point in the range of 0°–85° C. is prepared by polymerizing 20–80 parts by weight of a terpene hydrocarbon monomer or mixtures of the same with 80 to 20 parts by weight of an oligomer of a cyclic monoterpene hydrocarbon in the presence of a Friedel-Crafts catalyst (i.e. aluminum chloride).

U.S. Pat. Nos. 4,165,301 to Wiegers et al. and 4,170,576 to Hall et al disclose use of terpene dimers in perfumery processes and products. In Wiegers a single phase liquid perfumery composition is provided including a natural or synthetic perfume oil and a reaction product selected from the group consisting of dimerization products of monocyclic terpenes (i.e. alpha-pinene, beta-pinene, d-limonene, etc.) or hydrogenated dimerization products of the same monocyclic terpenes or mixtures thereof.

In Hall et al. the perfume compositions include a dimerization product of an α-methyl styrene or a methyl or other C2–4 lower alkyl homologue and a reaction product selected from the group consisting of dimerization or hydrogenation products of twenty carbon atom-containing terpenes.

U.S. Pat. No. 4,399,249 to Bildusas et al. discloses pressure sensitive adhesive compositions that are resealable to polyethylene surfaces at room temperature. The composition includes 20–60 wt. % of a block copolymer; 5–50 wt. % of an end block modifying resin; 20–60 wt. % of a plasticizing process oil and less than 14 wt. % of a mid block modifying tackifying resin.

U.S. Pat. No. 4,922,047 to Chen et al. discloses a process for producing lube oil traction fluid. The process requires reacting bicyclic or monocyclic terpene over a zeolite catalyst (hydrated aluminum and calcium or sodium silicates) at elevated temperature to obtain a high boiling liquid product comprising dimer or trimer of the bicyclic or monocylic terpene.

U.S. Pat. No. 5,092,907 to Riblet et al. discloses a liquid colorant dispersion incorporated into plastic materials to produce a homogeneous coloration. The dispersion includes at least one colorant material contained in a vehicle comprised of a dimer of α-pinene.

From the prior art mentioned utilization of terpene polymers as components of hot melt coating compositions (Sellers '136, Booth), as an adhesive (Bildusas) as tackifiers and plasticizers (Todd, Uchigaki), as solvents (Sellers '893) and as a colorant material (Riblet) are shown. However, in these applications use of a terpene polymer is with additional polymer components. None of these references disclose the particular terpene dimer compositions of the present invention which are substantially free of higher terpene oligomers and unexpectedly were found to dry into a hard, tack free film without additional components.

Being derived from naturally occurring monoterpenes the compositions of the invention are non-toxic and thus has advantage over solvents such as toluene or mineral spirits that are used in many coating applications to reduce formulation viscosity. The process of the invention is advantageous over J. J. Ritter's procedure and produces terpene dimer compositions prepared by a condensation process which results in a composition that is substantially free of higher terpene oligomers.

Accordingly, it is a broad object of the invention to provide terpene dimer compositions which are substantially free of higher terpene oligomers.

A more specific object of the invention is to provide terpene dimer compositions comprising a terpene dimer which is derived from naturally occurring monoterpenes, or mixtures thereof.

Another object of the invention is to provide terpene dimer compositions which dry into a hard, tack free film upon exposure to air.

Another more specific object of the invention is to provide terpene dimer compositions for use as a diluent, solvent or component in coating, adhesive, alkyd or ink formulations, as an environmentally safe non-toxic material.

Another object of the invention is to provide a process for manufacture of terpene dimer compositions which are substantially free of higher terpene oligomers.

A further specific object of the invention is to provide a process for producing terpene dimer compositions by a condensation reaction of naturally occurring monoterpenes, or mixtures thereof.

DISCLOSURE OF THE INVENTION

In the present invention, these purposes, as well as others which will be apparent, are achieved generally by providing terpene dimer compositions, derived from monoterpenes, which are substantially free of higher terpene oligomers.

The compositions of the invention comprise a terpene dimer having the molecular formula $C_{20}H_{32}$ and contain at least one double bond. The terpene dimer comprises isomers having the molecular formula $C_{20}H_{32}$ and includes tricyclic structures, bicyclic structures, and/or monocyclic structures.

In an alternate embodiment, the compositions in addition to the terpene dimer include uncondensed monoterpenes and monomeric by-products. The uncondensed monoterpenes are isomers of the monoterpenes used in the preparation of the terpene dimer. The monomeric by-products are generally non-terpene materials, such as cymene, formed during the preparation of the dimer. The uncondensed monoterpenes and the monomeric by-products have molecular formulas of $C_{10}H_{14}$, $C_{10}H_{16}$ or $C_{10}H_{18}$.

The compositions provided by the invention process are all substantially free of higher terpene oligomers having molecular formulas greater than $C_{20}H_{32}$. Generally, the higher terpene oligomers are present in the compositions in amounts less than 15%, and preferably less than 5%.

The terpene dimer compositions of the invention are derived from a monoterpene, or mixtures thereof, having the molecular formula of $C_{10}H_{16}$. Preferably the monoterpenes are naturally occurring monoterpenes selected from the group consisting of alpha pinene, beta pinene, limonene, or other monoterpenes containing at least one double bond.

Generally, the terpene dimer compositions are produced by preparing a mixture including at least one monoterpene having the molecular formula $C_{10}H_{16}$ and an inorganic acid. Process and reaction conditions are controlled so that the mixture undergoes a condensation reaction that results in substantially complete dimerization of the terpene monomers. Concentrations of the inorganic acid and temperature conditions of the reaction are adjusted to yield maximum production of the terpene dimer. The resulting composition is substantially free of higher terpene oligomers having molecular formulas greater than $C_{20}H_{32}$.

The condensation reaction produces an organic layer and an aqueous layer. The aqueous layer includes the inorganic acid which is selected from the group consisting of phosphoric acid, other phosphorous acids and sulphuric acid. This aqueous layer is separated off from the organic layer, and the inorganic acid may be reused for subsequent condensation reactions.

The organic layer includes the terpene dimer as well as uncondensed monoterpenes and monomeric by-products. This layer may be subjected to further process steps including distillation to remove the uncondensed monoterpenes and monomeric by-products.

Preferred applications of the compositions of the invention include utilization as a diluent, solvent, or component in coating, adhesive, alkyd or ink formulations. In particular, a preferred application includes the terpene dimer compositions blended with a polyterpene resin for use as an agricultural sticker to adhere materials, such as pesticides, to plants. Advantageously the invention provides terpene dimer compositions that dry into a hard, tack free film upon exposure to air and provide an environmentally safe non-toxic material.

Other objects, features and advantages of the present invention will be apparent when the detailed description of the preferred embodiments of the invention are considered.

DETAILED DESCRIPTION OF THE PREFERRED EMBODIMENTS

Figure 1:
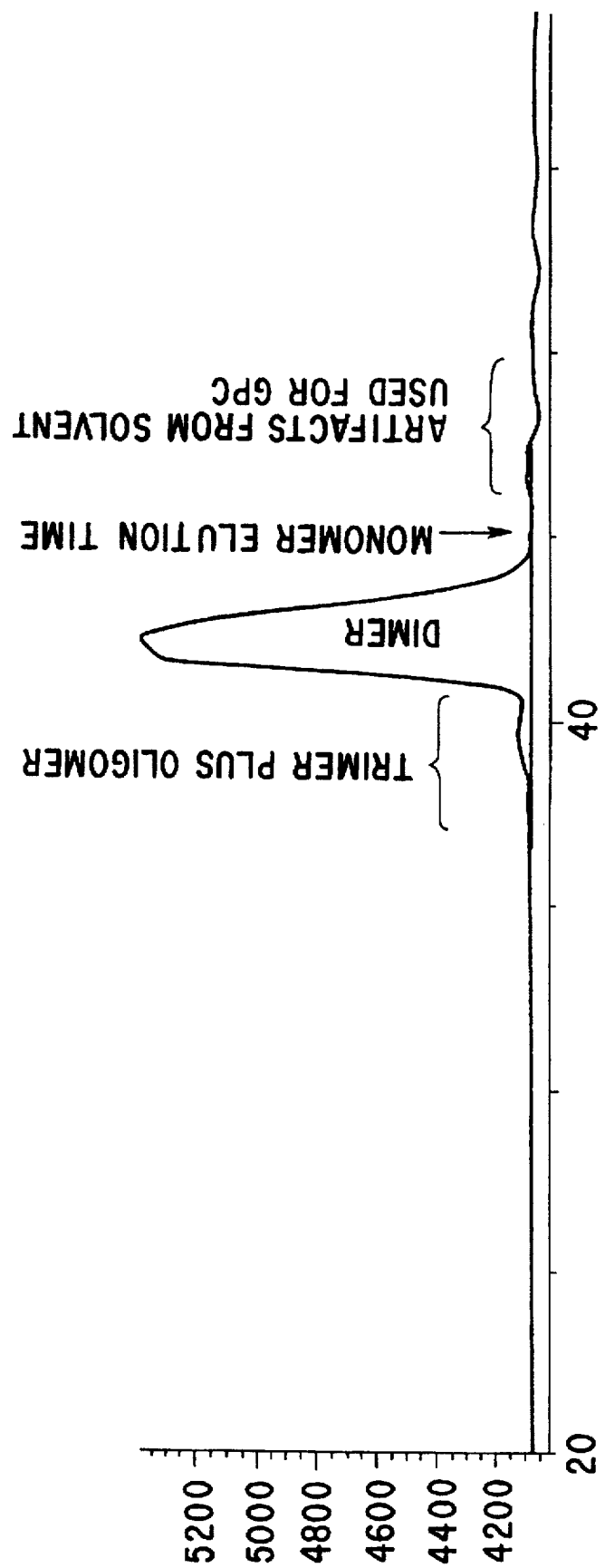
FIG. 1 is the Gel Permeation Chromatogram ("GPC") of the terpene dimer composition made in accordance with EXAMPLE I.

In accordance with the present invention terpene dimer compositions are provided which comprise a terpene dimer having the molecular formula $C_{20}H_{32}$ and contain at least one double bond, derived from monoterpenes having the molecular formula $C_{10}H_{16}$. The compositions are substantially free of higher terpene oligomers having molecular formulas greater than $C_{20}H_{32}$.

The terpene dimer comprises isomers having the molecular formula $C_{20}H_{32}$ and includes tricyclic structures, bicyclic structures and/or monocyclic structures as illustrated below.

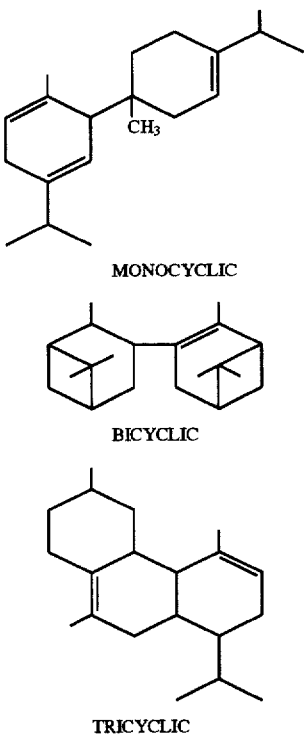

MONOCYCLIC

BICYCLIC

TRICYCLIC

In an alternate embodiment, the compositions in addition to the terpene dimer include uncondensed monoterpenes and monomeric by-products. The uncondensed monoterpenes are isomers of the monoterpenes used in the preparation of the terpene dimer. The monomeric by-products are generally non-terpene materials, such as cymene, formed during the preparation of the dimer. The uncondensed monoterpenes and monomeric by-products have molecular formulas of $C_{10}H_{14}$, $C_{10}H_{16}$ or $C_{10}H_{18}$.

The terpene dimer compositions of the invention are derived from a monoterpene, or mixtures thereof, having the molecular formula of $C_{10}H_{16}$. Preferably the monoterpenes are naturally occurring monoterpenes selected from the group consisting of alpha pinene, beta pinene, limonene, or other monoterpenes containing at least one double bond. The most preferred monoterpene used in the invention process is alpha pinene.

Generally, the terpene dimer compositions are produced by preparing a mixture including at least one monoterpene having the molecular formula $C_{10}H_{16}$ and an inorganic acid. The mixture is prepared by adding the monoterpene to the inorganic acid. Preferably 1.0 parts by weight of the monoterpene is combined with at least 0.3 parts by weight of the inorganic acid, preferably 0.6 parts by weight. It is advantageous to use a higher ratio of monoterpene to inorganic acid.

Alpha pinene is the preferred material used to make the terpene dimer using the phosphoric acid process of the invention. However, beta pinene, limonene and other monoterpenes containing multiple double bonds are suitable raw materials for this process. The resulting dimer from these materials would have similar bodying or drying performance.

The inorganic acid is selected from the group consisting of phosphoric acid, other phosphorus acids and sulphuric acid. Concentrations of the acid may vary and in connection with the temperature control the rate of reaction. Preferably, 85% phosphoric acid is used, however, 75% phosphoric acid produces a high dimer product as well.

The mixture is reacted at temperatures in the range of 25°–120° C., preferably 90°–120° C. At higher temperatures the reaction proceeds faster. Addition of a surfactant such as non-ionic Igepal® CO-630, available from Rhone-Poulenc, GAF Chemicals Group, 1361 Alps Road, Wayne, N.J., 07470, significantly speeds up the reaction. Other surfactants including anionic and cationic agents may be used. However, in the preferred procedure this component is optional, since the separation of the phosphoric acid from the organic layer is simpler without its inclusion.

The reaction is preferably conducted in an inert atmosphere, i.e. a nitrogen blanket, carbon dioxide, etc., to prevent oxidation. Oxidation reactions lead to coloration of the resulting compositions which may not be desired.

The condensation reaction results in substantially complete dimerization of the terpene monomers. Concentrations of the inorganic acid and temperature conditions of the reaction are adjusted to yield maximum production of the terpene dimer.

The condensation reaction produces an organic layer and an aqueous layer. The aqueous layer includes the inorganic acid. This aqueous layer is separated off from the organic layer, and the inorganic acid may be reused for subsequent condensation reactions.

The organic layer includes the terpene dimer as well as uncondensed monoterpenes and monomeric by-products. This layer may be subjected to further process steps including distillation to remove the uncondensed monoterpenes and monomeric by-products.

The resulting compositions are substantially free of higher terpene oligomers, generally less than 15%, and preferably less than 5%. Both compositions, with and without the uncondensed monoterpenes and monomeric by-products, were found to dry into a hard tack free film upon exposure to air. These compositions can be added as a diluent or solvent to a material to reduce the viscosity of the material. The compositions also may be added as a component in coating, adhesive, alkyd or ink formulations where film bodying, viscosity increase or drying is beneficial or essential.

The following examples illustrate various aspects of the invention but are not to be interpreted as limiting it. In EXAMPLES I to VI, terpene dimer compositions were prepared from monoterpenes, i.e. alpha pinene. In EXAMPLE VII, smears of the terpene dimer compositions were tested to examine how oily it felt and for its utility as a solvent for clean-up applications and other uses. In observations the smears hardened into tack-free films upon exposure to air.

EXAMPLE I

Experiment 1—Process for Preparation of the Terpene Dimer

Preparation of the terpene dimer composition was made by the following process from alpha pinene (Acintene A®, available from Arizona Chemical Company, 101 E. Business 98, Panama City, Fla., 32401-5294).

Phosphoric acid (85% grade) in the amount of 0.6 parts by weight (180 grams) is placed in a flask fitted with a thermometer, agitator and nitrogen inlet system to exclude air. This acid is heated to 90° C. Alpha pinene, 1.0 parts (300 grams) is added over two hours, controlling the temperature to within two degrees of 90° C. There is a slight exotherm during the addition of the alpha pinene. This mixture is held at 90° C. under agitation.

Samples were removed periodically during the reaction for analysis. Each sample was washed with dilute potassium carbonate to insure that the reaction was quenched. The extent of dimerization was followed by means of a 100° C. non-volatiles test with the results listed below. The 100° C. non-volatiles test is run by placing one gram of the sample in a two inch diameter flat bottom aluminum pan. The sample is placed on a 100° C. steam plate for one hour and the percent non-volatiles is computed from weight the loss.

EXTENT OF DIMERIZATION
EXAMPLE I - Experiment 1

| REACTION TIME, hr. (From point alpha pinene added) | Non-volatiles 100° C. % |
|---|---|
| 2 | 27 |
| 4 | 37 |
| 10 | 64 |
| 21 | 74 |

By the 23 hour the condensation reaction of the monoterpenes has been substantially completed. At this point the agitator was stopped and the bottom layer of phosphoric acid was drained off. Separation of this phosphoric layer from the organic layer is relatively quick and simple. The top organic layer was washed with dilute potassium carbonate and twice with distilled water.

The monoterpene portion (that which did not condense to form dimer and oligomer) was distilled off at 100 mm pressure from the mixture by gradually raising the temperature of the material up to 244°–248° C. The gravimetric yield of oil remaining after the volatiles were removed was 75 weight percent. Gel permeation chromatography ("GPC") was used to measure the quantity of dimer and oligomer remaining. The oligomer referred to herein is that material of higher molecular size than dimer, (greater than $C_{20}H_{32}$), and is believed to be mostly trimer and tetramer. Two GPC columns in series with tetrahydrofuran at 0.4 ml/min. were used for the analysis. A response factor of one was assumed on all peaks, thus area integration was used to assess the percentage of components. The GPC columns used were Waters Microstyragel™, 500 angstroms and 1000 angstroms, available from Waters Associates, Millipore Incorporated, Milford, Mass. Model R401 Differential Refractometer was the detector used to determine the quantity of components eluting from the columns. See FIG. 1.

The GPC of the 75% material remaining after the distillation indicated the composition 95.3% dimer and 4.7% oligomer with no detectable monomer. This low oligomer content is unique to the invention process and discussed in more detail in EXAMPLE II.

Experiment 2—Larger Scale Preparation of the Terpene Dimer Composition

The procedure in Experiment 1 was repeated on a larger scale using 3500 lb. Acintene A® with similar results. Analytical properties of the compositions which resulted in both experiments are listed in the tables below. In particular, TABLE I illustrates the terpene dimer plus monomer mixture prior to distillation, TABLE II is the composition after distillation and TABLE III is the monoterpene mixture from the distillation.

As noted in the tables below, "ASTM" refers to the American Society of Testing Materials standard procedures.

The Volatile Organic Compounds ("VOC") of the mixtures were determined by ASTM D2369-81, (Reference: United States Bureau of National Affairs, Inc. Federal Regulations, 120:1306 Part 60, Appendix A, Method 24).

The value for the setaflash was determined by measuring the flashpoint by setaflash closed cup tester, ASTM D3278-87, D3828-81.

The Gardner Color value (ASTM D1544-80) is on a scale from 1 to 18, where 18 is dark and 1 is light. For example, 3– is slightly lighter than 3.

TABLE I

TERPENE DIMER PLUS MONOMER MIXTURE
(prior to distilling off remaining monoterpenes)

| ANALYTICAL PROPERTIES | VALUE |
|---|---|
| COLOR (GARDNER) ASTM D1544-80 | 3 – |
| KAURI BUTANOL VALUE (KB) (solvency) ASTM D1133-86 | 49 |
| VOC | 62% |
| VOLATILES (230° C. 0.15 mm) | >99% |
| SETAFLASH | 145° F. |
| VISCOSITY (25° C. BROOKFIELD, LVT Viscometer #2 spindle) | 13 cP |
| ODOR (non-objectionable) | WOODY |

In TABLE I, the value for the volatiles of the mixture was determined by measuring the amount which volatilizes on exposure of a 0.15 gm sample to 230° C. at 0.15 mm pressure.

The KB value of the terpene dimer plus monomer mixture indicates the compositions ability to be utilized as a solvent in various applications. The high level of volatiles present indicates that there are low amounts of high molecular weight materials present in the composition. The setaflash value indicates that the composition is not classified as flammable and the low viscosity allows easy handling.

TABLE II

TERPENE DIMER
(after monomer is distilled off)

| ANALYTICAL PROPERTIES | VALUE |
|---|---|
| COLOR (GARDNER) ASTM D1544-80 | 3 + |
| KAURI BUTANOL VALUE (KB) (solvency) ASTM D1133-86 | 45 |
| VOC (EPA Method 24) | 28% |
| VOLATILES (residual monomer) | 70 ppm |
| SETAFLASH (noncombustible) | 308° F. |
| VISCOSITY (25° C. BROOKFIELD, LVT Viscometer #2 spindle) | 134 cP |
| ODOR (non-objectionable) | faint oily odor |

The value for the volatiles of this composition was determined by a different method from that used in the terpene dimer plus monomer mixture. The residual monomer was determined by quantitative GLC analysis. The volatile oils are solvent extracted and the oils present are quantitatively determined using an internal standard by capillary GLC. Column Supelcowax™ ID capillary column, 30 m×0.25 mm ID, 0.25 micron film thickness, temperature 60° C. for 2 min., ramp 10° C./min to 150° C. The columns used are available from Supelco, Inc., Supelco Park, Bellefonte, Pa., 16823.

The Gel permeation chromatography indicates that in the terpene dimer composition the amount of trimer plus oligomer is approximately 2.4%. See FIG. 1.

Gas chromatography (GLC) analysis indicates that the terpene dimer is a complex mixture of at least 50 components. GLC/mass spectrophotometry of the mixture shows essentially all these components to have a molecular weight of 272 corresponding to $C_{20}H_{32}$, the condensation of two alpha pinene units.

Figure 3:
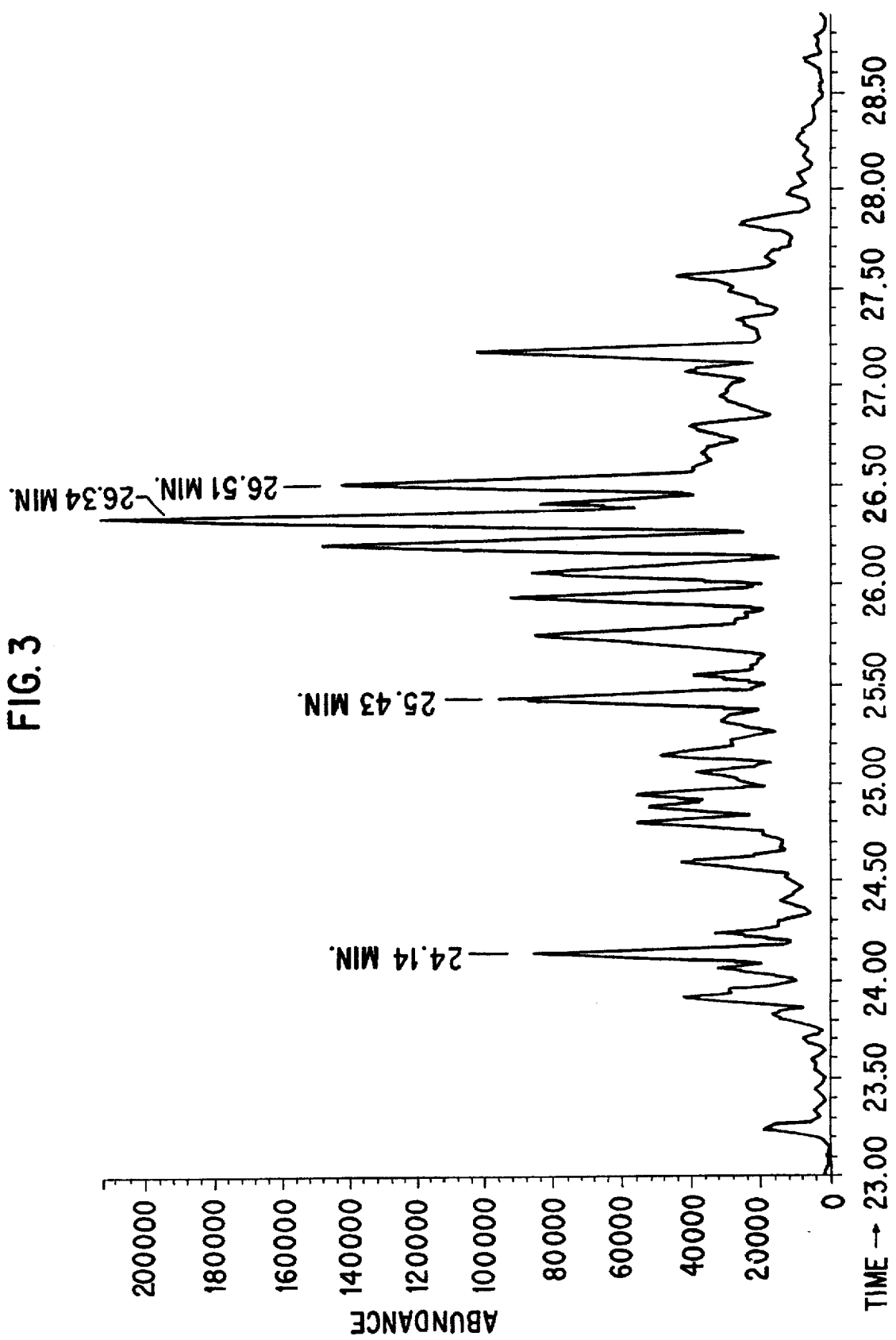
FIG. 3 is the Mass Spec Scan of the terpene dimer from EXAMPLE I (total ion count).
Figure 4:
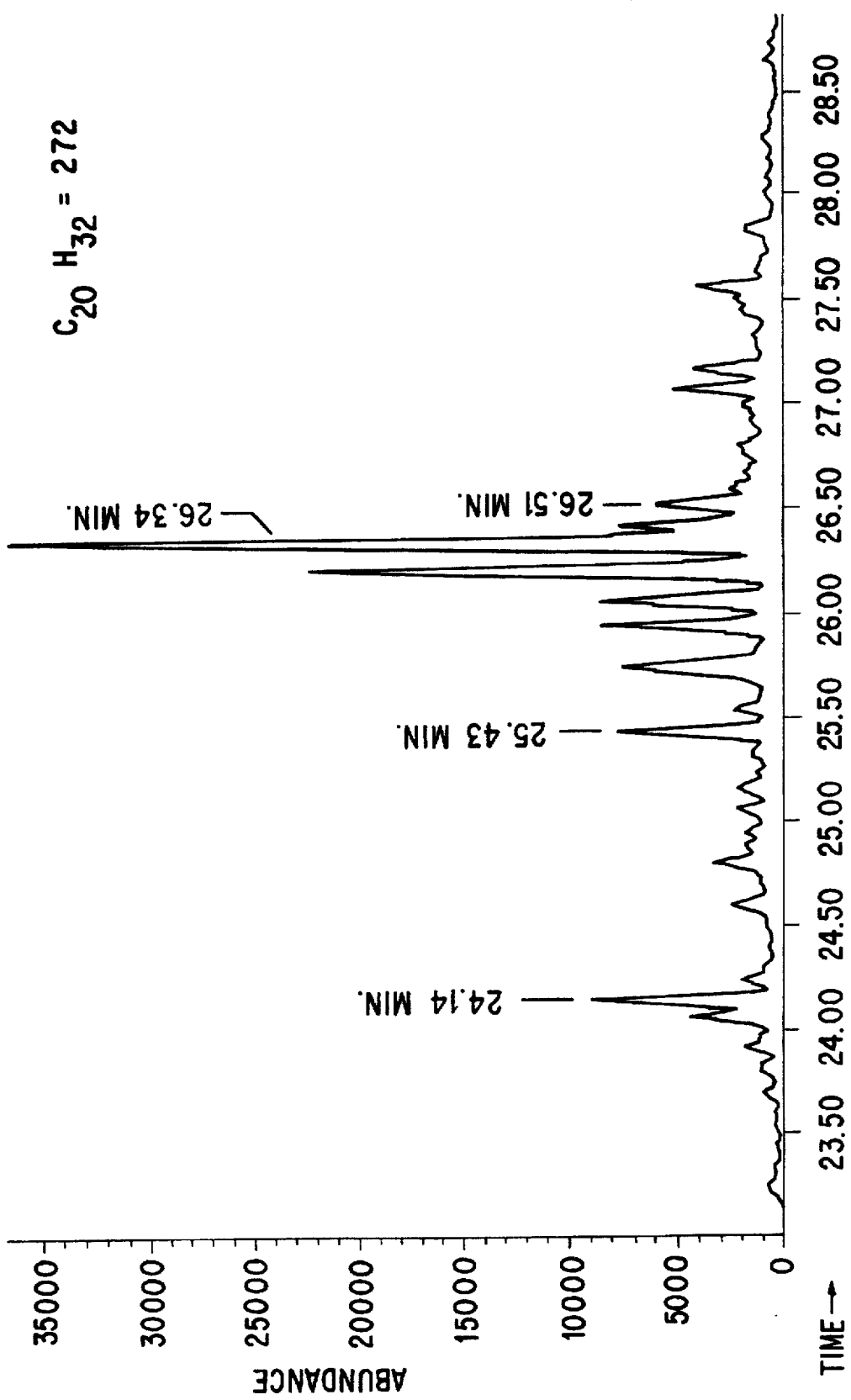
FIG. 4 is the Mass Spec Scan of the terpene dimer from EXAMPLE I (m/e 272 ion count).
Figure 5:
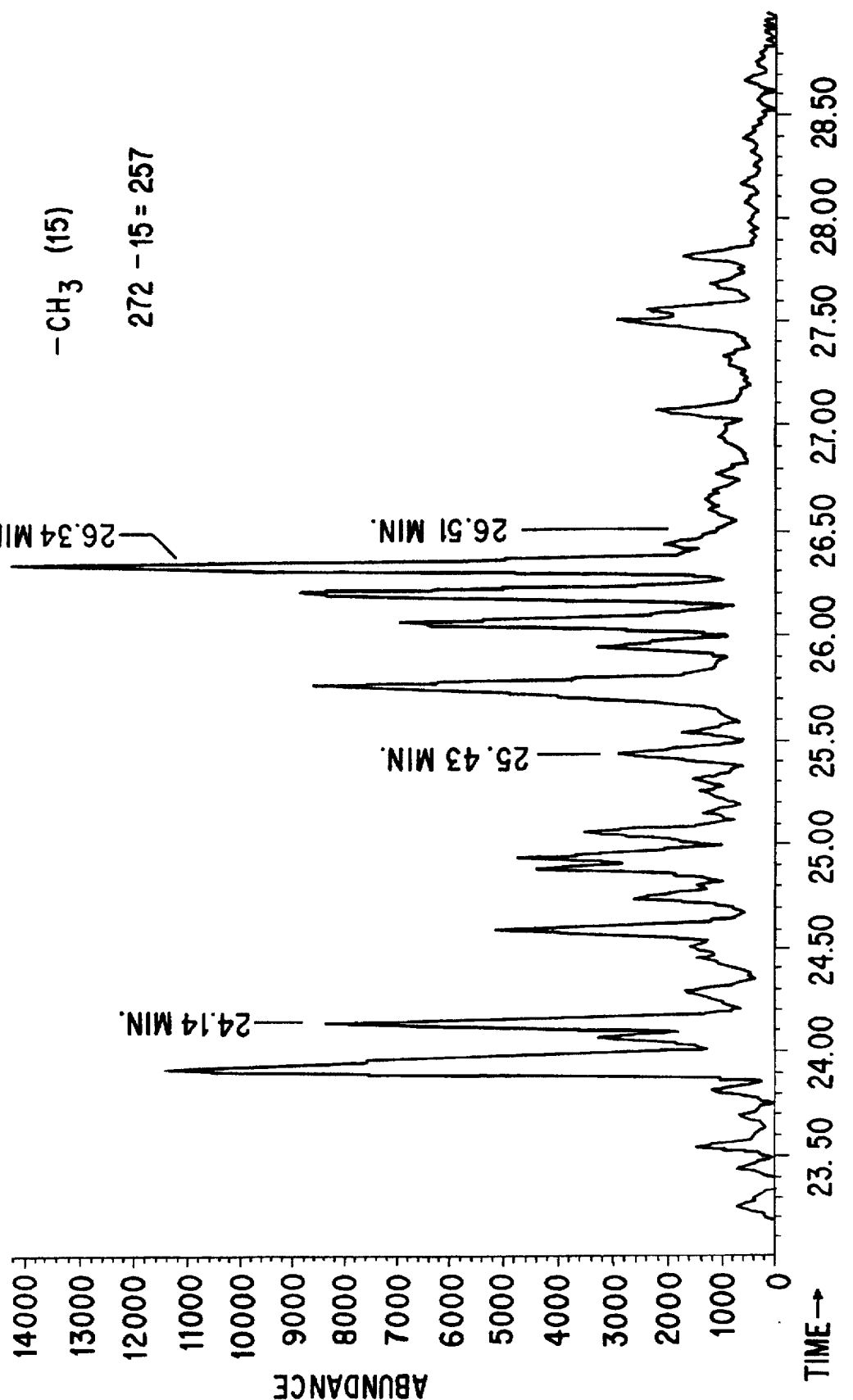
FIG. 5 is the Mass Spec Scan of the terpene dimer from EXAMPLE I (m/e 257 ion count).
Figure 6:
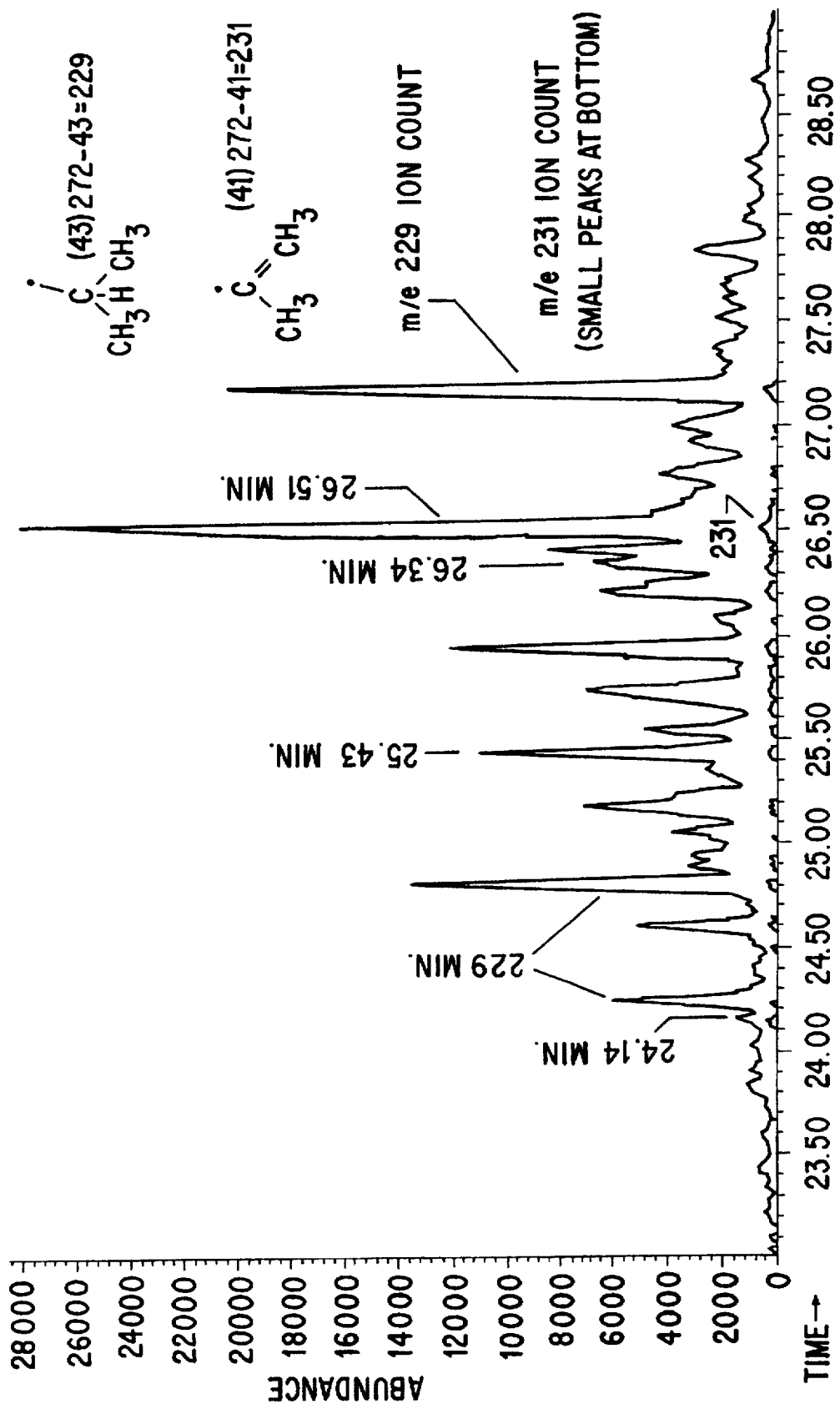
FIG. 6 is the Mass Spec Scan of the terpene dimer from EXAMPLE I (m/e 231 and 229 ion counts).
Figure 7A:
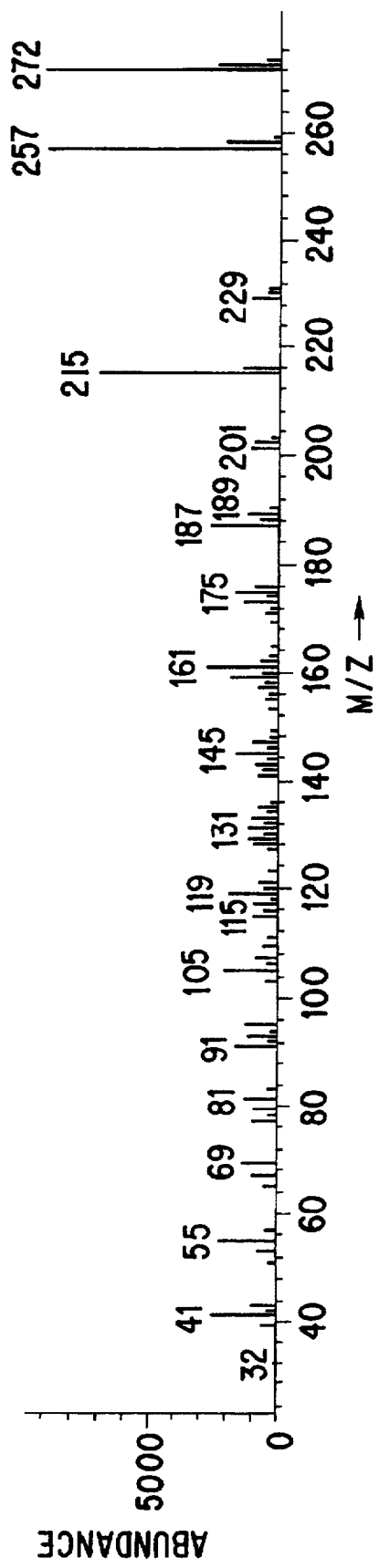
FIG. 7A, B, C and D are the Mass Spec Fragmentation Patterns for some of the main peaks from the GLC of the terpene dimer from EXAMPLE I at 24.14 min, 25.43 min, 26.34 min and 26.51 min, respectively.
Figure 7B:
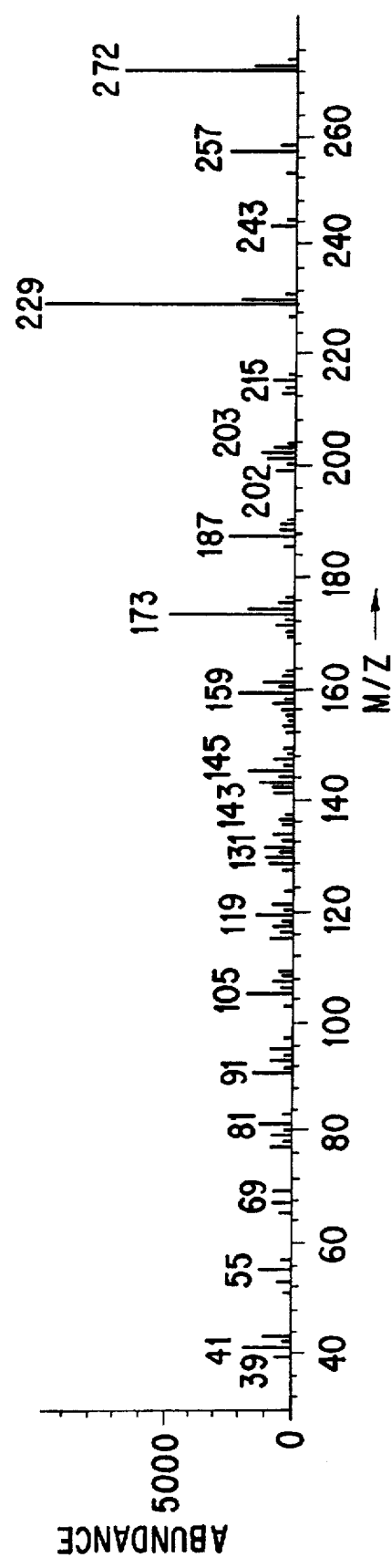
Figure 7C:
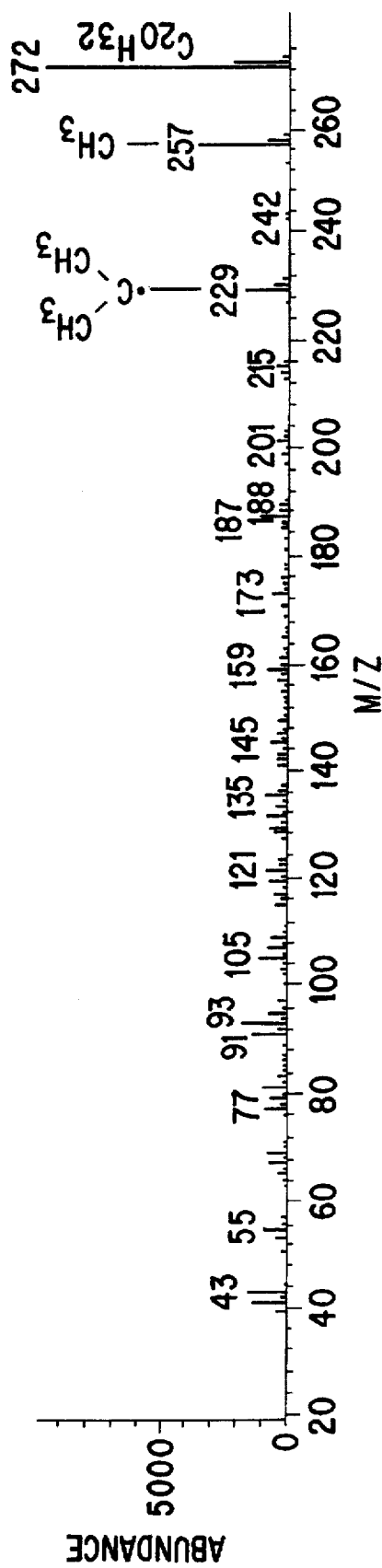
Figure 7D:
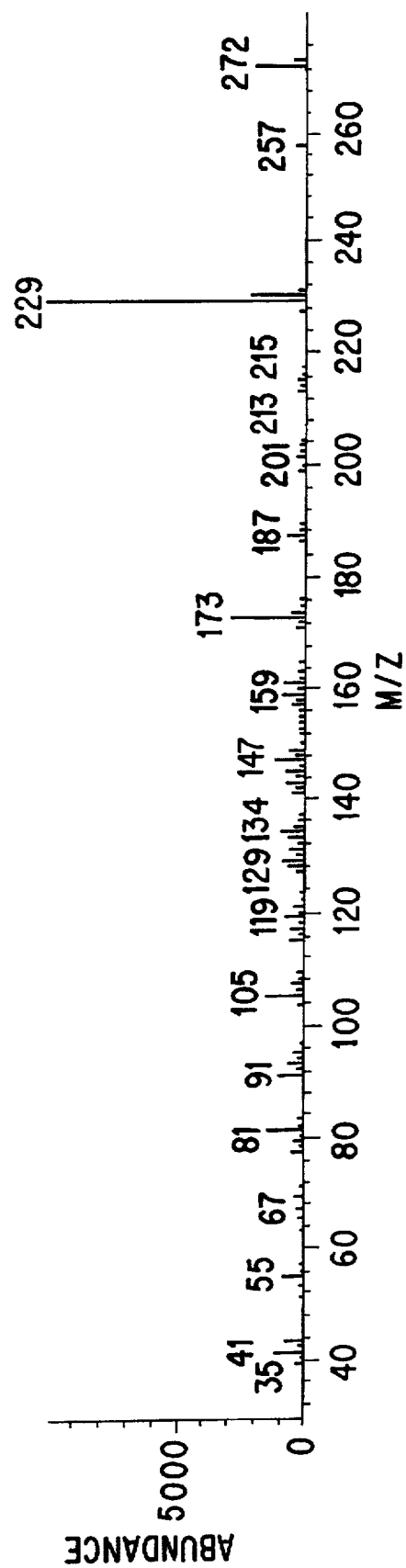

FIGS. 3 to 7 illustrate the results of the structural studies of the terpene dimer compositions. A GC/Mass spec scan of the total ion count of the terpene dimer composition is shown in FIG. 3. (DP1 Column, 0.25 mm×60 m, 0.25 micron film thickness, available from J&W Scientific, 91 Blue Avenue, Folsom, Calif., 95630.) The peaks clearly are dimer ($C_{20}H_{32}$) as can be seen from a m/e 272 ion count scan in FIG. 4. There are also minor concentrations of components having the structures $C_{20}H_{30}$ and $C_{20}H_{31}$. Nearly all of the components of the composition loose $CH_3$ as can be seen from the m/e 257 ion count scan in FIG. 5. On FIG. 6 is the ion count scan for loss of isopropyl and isopropenyl. There is no significant loss of isopropenyl from any of the components, thus this functionality is not expected in any of the components of the composition. On the other hand there is considerable loss of isopropyl. Fragmentation patterns for some of the main peaks from the GLC are shown in FIGS. 7A, 7B, 7C and 7D for reference.

Following the course of the condensation reaction by GLC it is observed that the alpha pinene rearranges to other monoterpenes and monomeric by-products during the dimerization reaction, all of which have $C_{10}H_{14}$, $C_{10}H_{16}$ and $C_{10}H_{18}$ molecular formulas. It is believed that it is these other monoterpene rearrangement products, primarily of the formula $C_{10}H_{16}$, such as limonene, which actually undergo the condensation reaction. Based on the number of dimer components, it is clear that there is more than one mechanism of dimerization. Possible mechanistic routes for dimer formation are shown below.

POSSIBLE CONDENSATION ROUTES

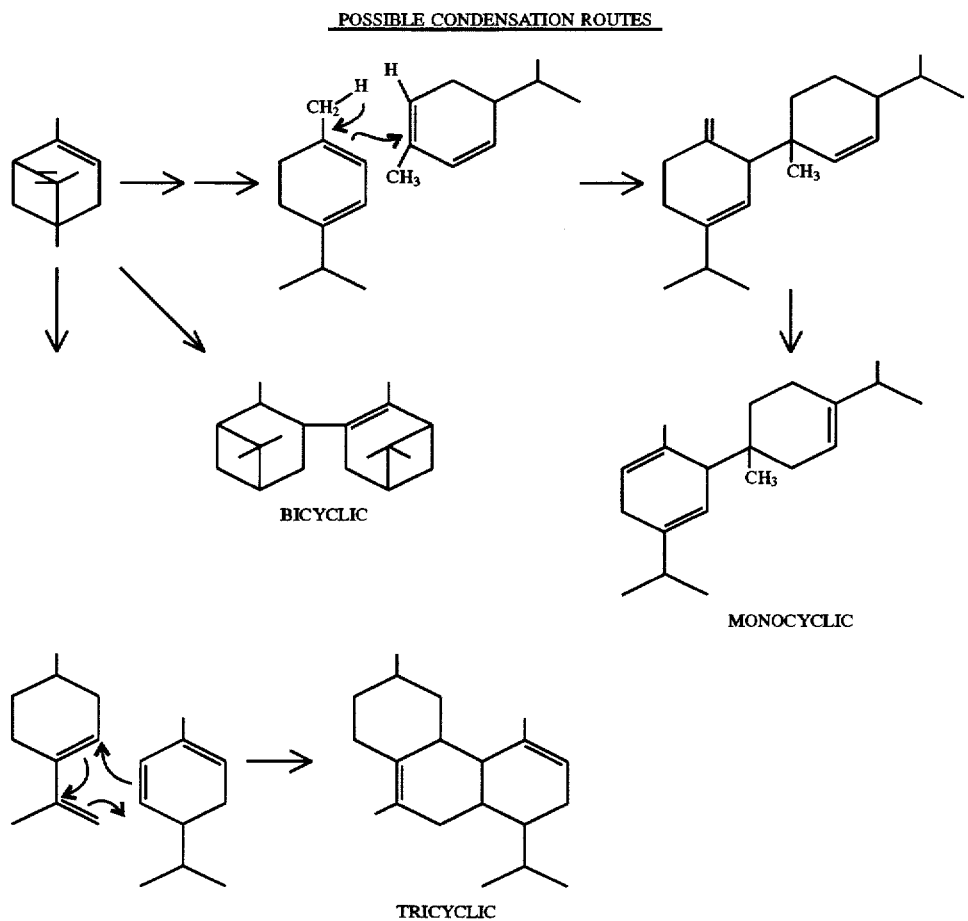

BICYCLIC

MONOCYCLIC

TRICYCLIC

From the condensation pathways shown the terpene dimer comprises isomers having the molecular formula $C_{20}H_{32}$ and includes tricyclic, bicyclic and/or monocyclic structures. These structures illustrated are representative and are not to be interpreted as limiting the structures formed. For instance, the tricyclic structures may include other phenanthrenes having other configurations and C═C locations. The monocyclic and bicyclic structures also include other isomers not shown. In addition, uncondensed monoterpenes and monomeric by-products are also produced during the condensation process and are not illustrated in the pathways.

From the structural studies conducted the terpene dimer contains at least one double bond and preferably multiple double bonds. The high drying rate of the compositions, shown in EXAMPLE VII, suggests a high level of double bond concentration. Thus it is believed there are less of the phenanthrene type (tricyclic) structures based on drying rate of the compositions.

TABLE III

| MONOTERPENE MIXTURE (monomer from distillation) | |
|---|---|
| ANALYTICAL PROPERTIES | VALUE |
| COLOR (GARDNER) | 1– |
| STEAM PLATE NON-VOLATILES (100° C.) | 5% |
| SETAFLASH | 118° F. |
| ODOR (non-objectionable) | WOODY |

The value for the volatiles of the monoterpene mixture from the distillation was determined by placing a 1 to 1½ gram sample in an 18 mm×60 mm aluminum weighing dish which was held on a steam plate (100° C.) for one hour. The percent weight loss was calculated and equated to "non-volatiles".

The uniqueness of the terpene dimer formed through the condensation reaction process of the invention results in a composition that is almost all dimer. Generally less than 15% and preferably less than 5%. Additional physical characteristics of the terpene dimer formed include a refractive index of 1.5178 at 30°. As stated in TABLE II the viscosity of the dimer at 25° C. is 134 cP. At other temperatures the viscosity is as follows: 30° C.—84 cP; 40° C.—36 cP and 50° C.—22 cP. An infrared scan showed no hydroxyl absorption in the 3000–4000 nm range. The terpene dimer also has excellent color stability. A sample held in air had a starting color of 4– and remained at 4– color after 3 hours at 105° C. under nitrogen. Under air the color dropped to only 5+.

EXAMPLE II

Comparison tests were conducted between the invention process and the process disclosed in the article by J. J. Ritter, "J. Am. Chem. Soc.", Vol.62, pp. 1508–09 (1940), for the preparation of acid-polymerized dipinene ("Ritter").

Following the procedure outlined in Ritter, 200 ml (338.2 gm) (2.93 mole) of 85% phosphoric acid was added into the same equipment arrangement as in Experiment 1 of EXAMPLE I. The temperature was controlled to 30° C. 200 ml of alpha pinene, Acintene A®, (170.7 gm) (1.25 mole) was added over 3½ hours. The mixture was held under agitation for 120 hr. at ambient temperature. Samples were removed after 24 and 120 hours for analysis by the 100° C. non-volatiles test and by GPC. Reaction time was from the point alpha pinene added. The results are listed below:

| GPC DATA - EXAMPLE II | | | | |
|---|---|---|---|---|
| Reaction Time, hr. | Non-volatiles 100° C., % | GPC Monomer % | GPC Dimer % | GPC Oligomer % |
| 24 | 62 | 21.8 | 60.9 | 16.9 |
| 120 | 73 | 8.1 | 77.8 | 13.6 |

The monoterpene portion, that did not condense, was distilled off as in EXAMPLE I. The gravimetric yield of the oil remaining after the volatiles were removed was 83 weight percent. Gel permeation chromatography (GPC) showed no monomer, 85.0% dimer and 15.0% oligomer.

The yield of dimer plus oligomer from this experiment is slightly higher than in EXAMPLE I (83% versus 75%). However there is a significant difference in the composition of the two products. EXAMPLE I contained 95.3% dimer and only 4.7% oligomer whereas in EXAMPLE II, following Ritter's practice, the dimer content was only 85% and the oligomer content was 15.0%.

The process of the invention provides an advantage over Ritter in the provision of compositions which are predominately dimer without the need to further distill the dimer away from the oligomer. The particular process conditions of the invention, including the specific temperature range of 90°–120° C., varying levels of phosphoric acid to monoterpene while maintaining a higher ratio of monoterpene to acid, the presence or absence of a surfactant, all resulted in mixtures which were low in oligomer content, similar to that found in EXAMPLE I, and less than the 15% using Ritters procedure.

EXAMPLE III

75% Phosphoric Acid, 90° C.

The same procedure as in EXAMPLE I (Experiment 1) was followed except that 75% phosphoric acid was used in place of 85% phosphoric acid. Samples were removed from the reaction and analyzed with the results listed below. The reaction time is determined from the point at which the alpha pinene was added.

| EXTENT OF DIMERIZATION EXAMPLE III | |
|---|---|
| Reaction Time, hour | Non-volatiles, 100° C., % |
| 5 | 14 |
| 10 | 23 |
| 22 | 38 |
| 46 | 52 |

Based on the non-volatiles data, it appears that the dimerization reaction proceeds at a slower rate than in EXAMPLE I. In EXAMPLE I after 21 hours the non-volatiles are 74% and in EXAMPLE II, after 22 hours the non-volatiles are only 34%.

EXAMPLE IV

75% Phosphoric Acid, 120° C.

A repeat of EXAMPLE III at 120° C. provided the following results.

| EXTENT OF DIMERIZATION EXAMPLE IV | |
|---|---|
| Reaction Time, hour | Non-volatiles, 100° C., % |
| 12 | 22 |
| 18 | 31 |
| 23 | 35 |

As illustrated the reaction using 75% phosphoric acid at 120° C. was slower than at 90° C.

EXAMPLE V

85% Phosphoric Acid, 100° C.

The process conditions in EXAMPLE I (Experiment 1) were repeated in two additional experiments using 85% phosphoric acid at 100° C. In the first experiment, after 23 hours, the non-volatiles content was 67% and in the second experiment, after 22 hours, the non-volatiles content was 69%.

5,723,709

13

This data indicates that the process at 90° C. results in a slightly higher yield than at 100° C. However, the yields at the higher temperature using 85% phosphoric acid are acceptable.

EXAMPLE VI

Recycled 85% Phosphoric Acid, 90° C.

The process conditions in EXAMPLE I (Experiment #1) were repeated except a used (recycled) 85% phosphoric acid was tested and the weight ratio of phosphoric acid to alpha pinene was reduced from 0.6/1.0 down to 0.3/1.0. After 21 hours the non-volatiles content was 61%. This result is slightly less than with use of the higher ratio of phosphoric acid to alpha pinene.

The 85% phosphoric acid could be reused repeatedly. Its strength does not go down but actually tends to increase about 2% with five reuses of the acid.

EXAMPLE VII

Drying Experiments With Terpene Dimer

The following experiments illustrate the drying ability of the terpene dimer and dimer and monomer mixture (prior to distilling off the remaining monoterpenes) from EXAMPLE I.

The terpene dimer plus a metallic drying agent, (2% of a cobalt, manganese drier, Mooney Chemical Co-Mn Lin-All P.I. Drier 907, O M Group, Inc.; OutoKumpu Chemicals, formerly Mooney Chemicals, Inc., 2301 Scranton Road, Cleveland, Ohio, 44113-4395), was spread on a glass plate as a one mil film by means of a draw-down bar. In 5 hours the film was nearly tack free by lightly brushing it with the finger. In a side-by-side experiment a draw-down was made with terpene dimer free of drier. After the five hour period it still remained tacky, even though it may have bodied slightly. The next morning both samples had dried to a tack free film.

In additional side-by-side experiments, a sample of a by-product oil from the production of styrenated polyterpene resins and a sample of an other dimer oil prepared by means of the ion exchange resin had been drawn down in one mil films. The film from the by-product oil from the production of styrenated polyterpene resins tended to bead up but there was no evidence of bodying. The other dimer oil prepared by means of the ion exchange resin as a one mil film slightly increased in viscosity, but still remained tacky.

As an alternate drying agent, tert-butyl-peroxy-2 ethyl hexanoate (0.05%) was added to the terpene dimer which was made by means of the phosphoric acid process (as in EXAMPLE I). This dried to a tack free film overnight.

Another series of eight drying experiments (Experiments #1–8) were conducted with the results detailed in TABLE IV below entitled "Drying Time Comparisons, One Mil Film Drawn on Mylar Film". The draw-downs for drying time studies were made on corona treated Mylar film. A one mil film was drawn using a PG&T #34 draw-down bar.

"Oil A" in TABLE IV, is a dimer oil prepared from an ion exchange resin process and contains one third trimer plus oligomer. Oil A dries more slowly than the terpene dimer (Experiment #7).

"Oil B" in TABLE IV, is a by-product oil from production of styrenated polyterpene resins. In Experiments #4 and #6, the oil does not appear to dry.

14

TABLE IV

DRYING TIME COMPARISIONS
ONE MIL FILM DRAWN ON MYLAR FILM

| Exp. # | MATERIALS | ONE HOUR | TWO HOURS | TWENTY TWO HOURS |
|---|---|---|---|---|
| 1 | LINSEED OIL+* TERPENE DIMER▲* | Linseed Oil less tacky | Same | Both samples dry to equal hardness; Both samples dry, tack-free films |
| 2 | LINSEED OIL+** TERPENE DIMER▲** | Linseed Oil less tacky | Not recorded | Both samples dry to equal hardness; Both samples dry, tack-free films |
| 3 | LINSEED OIL+ TERPENE DIMER▲ | Terpene Dimer less tacky | Terpene Dimer less tacky | Linseed Oil - wet film Terpene Dimer - dry, tack-free film |
| 4 | LINSEED OIL+ OIL B°° | Linseed Oil appeared less tacky | Linseed Oil appeared less tacky | Both samples - wet films |
| 5 | LINSEED OIL+ OIL A° | Oil A less tacky | Oil A less tacky | Linseed Oil - wet film Oil A - slightly tacky |
| 6 | TERPENE DIMER▲ OIL B°° | Terpene Dimer less tacky | Not recorded | Terpene Dimer - dry, tack-free film Oil B - wet film |
| 7 | TERPENE DIMER▲ OIL A° | Terpene Dimer less tacky | Not recorded | Terpene Dimer - dry, tack-free film Oil A - wet film |
| 8 | LINSEED OIL+ TERPENE DIMER▲▲ | Terpene Dimer mixture less tacky | Same | Linseed Oil - wet film Terpene Dimer mixture - tack-free film |

*Drier #907 at 2% level, Mooney Chemical, Co-Mn Lin-All P.I. Drier 907.
**Drier #72 at 2% level, Mooney Chemical, Cobalt Nap-All.
▲Terpene Dimer - prepared by invention process with phosphoric acid.
▲▲Terpene Dimer - terpene dimer plus uncondensed monomer mixture from invention process prior to distilling off remaining monoterpenes.
+Linseed Oil is alkali refined linseed oil from Welch, Holme & Clarke & Co., Inc.
°Oil A - dimer oil prepared from ion exchange resin process containing one third trimer plus oligomer.
°°Oil B - by-product oil from production of styrenated polyterpene resins, contains significant quantity of trimer plus oligomer.

From the results in TABLE IV it is shown that linseed oil, a common drying oil, and the terpene dimer both with added metallic drying agent, have similar drying properties (Experiments #1 and #2). However, in the absence of added metallic drying agent the terpene dimer dries overnight, but the linseed oil remains a wet film (Experiment #3). The terpene dimer plus monomer mixture reaction product prior to distilling off the remaining monoterpenes also dries (Experiment #8)

Alternate processes utilizing an ion exchange resin as a catalyst instead of phosphoric acid results in a terpene dimer oil that contains one third trimer plus oligomer. (Oil A) A GPC scan of the mixture prepared by the ion exchange procedure contained 34% oligomer and only 65% dimer. Terpene dimers which are prepared as a by-product oil from the production of styrenated polyterpene resins also contain a significant quantity of trimer plus oligomer, as much as 50%. (Oil B) In contrast, it is evident from these experiments that the terpene dimer from the phosphoric acid process of the invention has the right functionality for efficient drying upon exposure to air. As illustrated in TABLE V, both Oil A and Oil B dried more slowly, if at all, than the invention compositions. In addition, unlike the inorganic acid used in the invention process, the ion exchange resin cannot be recycled. Availability of product by the second alternate method is limited to the production of styrenated polyterpene resins.

Another series of experiments (Experiments #1–3) were performed and the results are listed in TABLE V below entitled "Weight Change of Films after Overnight Drying, One Mil Film Drawn on Glass Plates". In these experiments no drying agent was used. The procedure included one mil draw downs made on 80×10 mm glass plates using a PG&T #34 bar.

TABLE V

WEIGHT CHANGE OF FILMS AFTER OVERNIGHT DRYING ONE MIL FILM DRAWN ON GLASS PLATES

| Exp. # | MATERIALS | PLATE # 1 % WT. CHANGE | PLATE # 2 % WT. CHANGE | PLATE # 3 % WT. CHANGE |
|---|---|---|---|---|
| 1 | TERPENE DIMER▲ AMBIENT DRYING CONDITIONS | +14 | +12 | +12 |
| 2 | TERPENE DIMER▲ PLATES IN OVEN AT 80° C. | −63 | −62 | −48 |
| 3 | LINSEED OIL+ AMBIENT DRYING CONDITIONS | 0 | 0 | −3 |

▲Terpene Dimer - prepared by invention process with phosphoric acid.
+Linseed Oil is alkali refined linseed oil from Welch, Holme & Clarke & Co., Inc.

The terpene dimer film from the phosphoric acid process gained 12–14% in weight during overnight drying (Experiment #1). At 80° C. in an oven the film lost significant weight (Experiment #2). The linseed oil film at room temperature essentially did not change weight. This provides evidence that the terpene dimer at room temperature is not appearing to dry because of significant weight loss to a concentrated oligomer. On the other hand this indicates that the terpene dimer is drying or bodying at room temperature.

Figure 2:
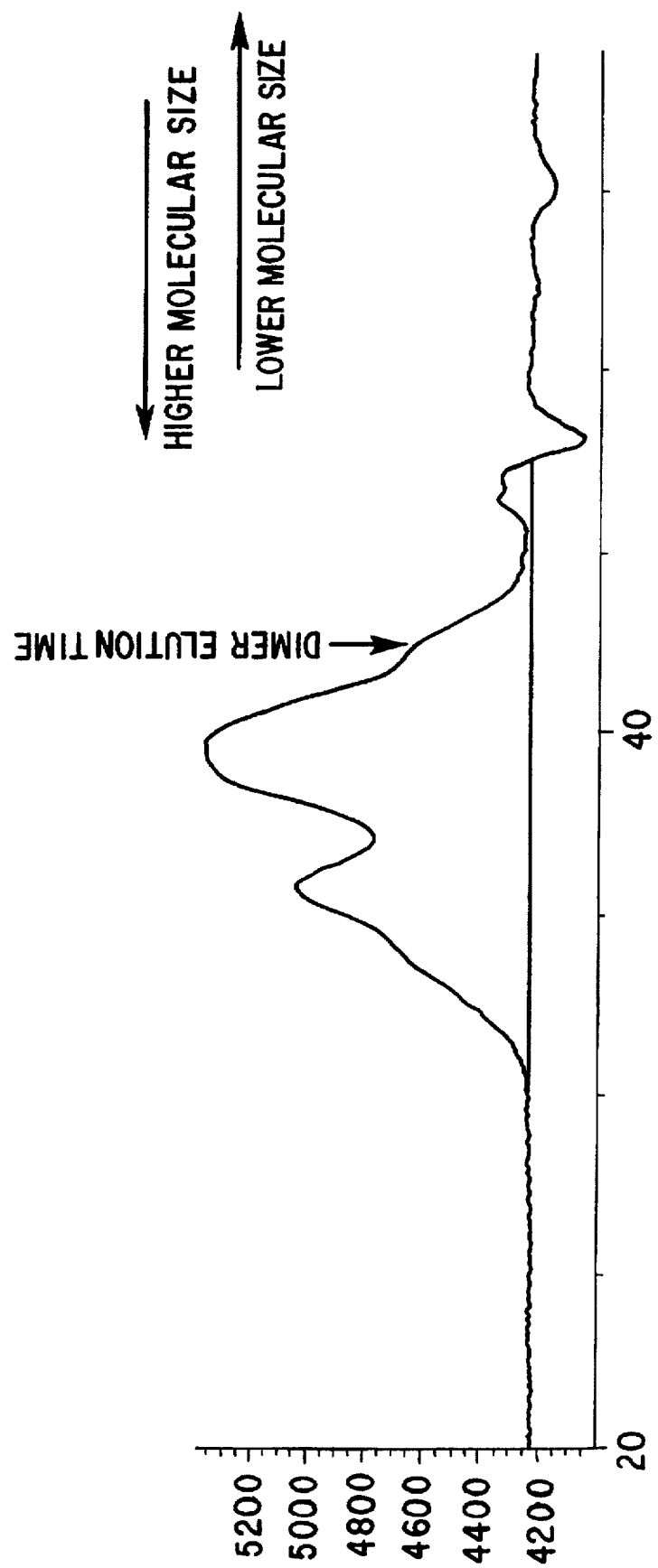
FIG. 2 is the GPC of a one mil terpene dimer film exposed to air for 15 days, from EXAMPLE VII.

FIG. 2 illustrates a GPC of a one mil film of the terpene dimer oil that was exposed to air (at ambient conditions) for 15 days. The GPC shows that the elution time for components of the composition that are of a higher molecular size is faster than for the components that are a lower molecular size.

Advantageously, the terpene dimer compositions of the invention are derived from naturally occurring monoterpenes and are essentially non-toxic. It is known that synthetic resins derived from alpha pinene are approved for human consumption in chewing gum base (See Code of Federal Regulations, 21 CFR 100.1, 172.623). Preferred applications of the terpene dimer compositions include utilization as a diluent, solvent or component in coating, adhesive, alkyd or ink formulations, as an environmentally safe non-toxic material. The absence of trimerized terpenes plus oligomers result in its low viscosity and its high flash point after or before the monoterpenes are distilled off are both advantageous properties. However, the primary unique attribute of the terpene dimer oil is that it will body upon exposure to air.

In particular, due to its low viscosity the terpene dimer oil can function as a diluent to reduce formulation viscosities. The compositions have major advantages over solvents such as toluene or mineral spirits that must be used in many coatings applications to perform the same function. The compositions are relatively non-volatile compared to mineral spirits. An alkyd formulation containing terpene dimer in place of mineral spirits would have reduced emissions and would contain an environmentally "green" solvent, but one that would body and air dry to become part of the film. The combination of low viscosity, solvency features plus the bodying are the compositions attributes.

It will be recognized by those skilled in the art that the low viscosity oil has wide application where film bodying, viscosity increase or drying is beneficial or essential. As an alternative to toluene or mineral spirits, the terpene dimer is an environmentally acceptable material for use as a solvent for clean up applications and advantageously provides a safe non-toxic material.

In side by side drying experiments comparing the dimer oil with linseed oil it was demonstrated that a film of the dimer oil exposed to air unexpectedly dried into a hard, tack free layer. Linseed oil without a metallic dryer added was inferior to the dimer oil (before or after the volatiles are distilled off) in drying. Linseed oil is common to paints, enamels and varnishes and an alternative derived from monoterpenes such as alpha pinene is unique.

Numerous modifications are possible in light of the above disclosure such as utilizing the dimer compositions in applications in place of linseed oil and also in combining the dimer compositions with a wide variety of additional components. For instance, the dimer compositions may be blended with polyterpene resins for use as an agricultural sticker to adhere materials to plants. Preferably 10 to 20% of a beta pinene polymer is blended with the terpene dimer composition which may be used as an agricultural sticker to adhere pesticides to plants.

Therefore, although the invention has been described with reference to certain preferred embodiments, it will be appreciated that other composite structures and processes for their fabrication may be devised, which are nevertheless within the scope and spirit of the invention as defined in the claims appended hereto.

We claim:

1. A process for the preparation of a terpene dimer composition comprising the sequential steps of:

preparing a mixture by adding at least one monoterpene having the molecular formula $C_{10}H_{16}$ to an inorganic acid; wherein 1.0 parts by weight of said monoterpene is combined with approximately 0.3 to 0.6 parts by weight of said inorganic acid;

reacting said mixture at temperatures in the range of 90°–120° C. to cause the condensation of said monoterpene into a terpene dimer having the molecular formula $C_{20}H_{32}$ and containing at least one double bond;

wherein the composition is produced without a distillation step and includes uncondensed monoterpenes, monomeric by-products having the molecular formulas $C_{10}H_{14}$, $C_{10}H_{16}$ or $C_{10}H_{18}$, and less than 15% of terpene oligomers having molecular formulas greater than $C_{20}H_{32}$.

2. The process according to claim 1, wherein the composition produced is further subject to a distillation step to remove said uncondensed monoterpenes and said monomeric byproducts.

3. The process according to claim 1, wherein said inorganic acid is selected from the group consisting of phosphoric acid, other phosphorus acids and sulfuric acid.

4. The process according to claim 1, wherein said inorganic acid remaining after said condensation reaction is recycled for use in additional condensation reactions.

5. The process according to claim 1, further comprising the addition of a surface active agent to the mixture to increase the reaction rate.

6. The process according to claim 1, wherein the composition includes isomers of the terpene dimer having the molecular formula $C_{20}H_{32}$.

7. The process according to claim 1, wherein said terpene dimer includes tricyclic structures, bicyclic structures, monocyclic structures and mixtures thereof.

8. The process according to claim 1, wherein said monoterpene used in the preparation of the composition is a naturally-occurring monoterpene selected from the group consisting of alpha pinene, beta pinene, limonene and monoterpenes containing at least one double bond.

9. The process according to claim 1, wherein said monoterpene used in the preparation of the composition contains at least two naturally-occurring monoterpenes selected from the group consisting of alpha pinene, beta pinene, limonene and monoterpenes containing at least one double bond.

10. A terpene dimer composition produced according to the process of claim 1, the composition having the property of drying into a hard tack-free film upon exposure to air.

11. The composition according to claim 10, wherein the composition includes isomers of the terpene dimer having the molecular formula $C_{20}H_{32}$.

12. The composition according to claim 10, wherein said terpene dimer includes tricyclic structures, bicyclic structures, monocyclic structures and mixtures thereof.

13. The composition according to claim 10, wherein the composition includes less than 5% of terpene oligomers having molecular formulas greater than $C_{20}H_{32}$.

14. The composition according to claim 10, wherein said monoterpene used in the preparation of the composition is a naturally-occurring monoterpene selected from the group consisting of alpha pinene, beta pinene, limonene and monoterpenes containing at least one double bond.

15. The composition according to claim 10, wherein the composition further comprises a polyterpene resin.

16. A terpene dimer composition produced according to the process of claim 2, the composition having the property of drying into a hard tack-free film upon exposure to air.

17. The composition according to claim 16, wherein the composition includes isomers of the terpene dimer having the molecular formula $C_{20}H_{32}$.

18. The composition according to claim 16, wherein said terpene dimer includes tricyclic structures, bicyclic structures, monocyclic structures and mixtures thereof.

19. The composition according to claim 16, wherein the composition includes less than 5% of terpene oligomers having molecular formulas greater than $C_{20}H_{32}$.

20. The composition according to claim 16, wherein said monoterpene used in the preparation of the composition is a naturally-occurring monoterpene selected from the group consisting of alpha pinene, beta pinene, limonene and monoterpenes containing at least one double bond.

21. The composition according to claim 16, wherein the composition further comprises a polyterpene resin.

* * * * *